(12) United States Patent
Tsuchiya

(10) Patent No.: US 6,905,521 B2
(45) Date of Patent: Jun. 14, 2005

(54) CUMULATIVE HAIR-DYEING TEMPORARY HAIR DYES AND PROCESS FOR PRODUCING THE SAME

(75) Inventor: Eiji Tsuchiya, Fujioka (JP)

(73) Assignee: Mitsubishi Pencil Kabushiki Kaisha, Tokyo (JP)

( * ) Notice: Subject to any disclaimer, the term of this patent is extended or adjusted under 35 U.S.C. 154(b) by 278 days.

(21) Appl. No.: 10/148,564

(22) PCT Filed: Dec. 15, 2000

(86) PCT No.: PCT/JP00/08921

§ 371 (c)(1),
(2), (4) Date: Jun. 3, 2002

(87) PCT Pub. No.: WO01/43707

PCT Pub. Date: Jun. 21, 2001

(65) Prior Publication Data

US 2003/0066142 A1 Apr. 10, 2003

(30) Foreign Application Priority Data

Dec. 16, 1999 (JP) ............................................. 11-357891

(51) Int. Cl.⁷ ................................................. A61K 7/13
(52) U.S. Cl. ....................... 8/405; 8/455; 8/463; 8/552; 8/557; 8/558; 8/581; 132/212; 132/219; 132/221; 132/265; 132/272
(58) Field of Search ............................ 8/405, 455, 463, 8/552, 557, 558, 581; 132/212, 219, 221, 265, 272

(56) References Cited

U.S. PATENT DOCUMENTS 5,601,620 A * 2/1997 Ishikawa ........................ 8/405

FOREIGN PATENT DOCUMENTS

| EP | 918 069 A1 | 5/1999 |
| JP | 2-27968 B2 | 6/1990 |
| JP | 6-271427 | 9/1994 |
| JP | 4-4882 | 2/1996 |
| JP | 10-273431 A | 10/1998 |
| JP | 11-171741 | 6/1999 |

* cited by examiner

Primary Examiner—Brian P. Mruk
Assistant Examiner—Eisa Elhilo
(74) Attorney, Agent, or Firm—Burns, Doane, Swecker & Mathis, LLP

(57) ABSTRACT

Disclosed are a cumulative hair-dyeing temporary hairdye comprising 0.01 to 3% by weight of an acid dye as a colorant, 0.1 to 10% by weight of a nonionic or anionic silicone base resin, 3 to 20% by weight of a hair-dyeing aid, 30 to 80% by weight of a lower alcohol and 5 to 50% by-weight of water and having a pH of 2 to 5 and a viscosity of 100 mPa·s or less and a production process for a cumulative hair-dyeing temporary hairdye, wherein the respective components are blended in such an order that at least a nonionic or anionic silicone base resin and a lower alcohol are mixed to prepare a vehicle, and then the other components are blended therewith and stirred.

6 Claims, No Drawings

US 6,905,521 B2

CUMULATIVE HAIR-DYEING TEMPORARY HAIR DYES AND PROCESS FOR PRODUCING THE SAME

TECHNICAL FIELD

The present invention relates to a cumulative hair-dyeing temporary hairdye requiring no washing of the hair immediately after use and having a function to gradually dye the hair with repeating the use.

BACKGROUND ART

Various hairdyes have heretofore been used, which are classified into a permanent hairdye, a semi-permanent hairdye and a temporary hairdye from the viewpoint of persistency of hair dyeing. Among these classifications, oxidation dyes and acid dyes are used for permanent hairdyes and semi-permanent hairdyes respectively. The hair dyeing effect thereof is highly persistent, but preparation before hair dyeing and applying work of the liquids are complicated, and they are so short of convenience in an aspect that the hair has to be washed immediately after use.

In comparison with these hairdyes, so-called temporary hairdyes which temporarily color the hair with pigments are easy to use and can easily be washed away by washing the hair with a shampoo, and therefore they have been used for partially providing a mesh or dyeing white hair on the borders of the hair. Although the fact that they are easily washed-away by washing the hair is the characteristic of such temporary hairdyes and is related to simple usage, it is given as an unsatisfactory factor that they are extremely short of persistency as compared with other hairdyes.

A hairdye which solves this unsatisfactory factor is disclosed in Japanese Patent Publication Hei 2-27968, but it has the problems that the colorant secondarily stains a contacted matter when contacted in the state that the hair is not washed after dyeing and that in addition thereto, the hairdye flows away because of a poor water resistance thereof when wetted with water to stain other matters. Further, disclosed in Japanese Patent Application Laid-Open No. Hei 10-273431 is a hairdye prepared by blending an acid dye, a pigment and an amphoteric polymer resin having a betaine group in a specific proportion, and disclosed in Japanese Patent Application Laid-Open No. Hei 11-171741 is a temporary hairdye which is prepared by blending a block copolymer comprising a cyclohexane segment and an anionic monomer unit as structural components and which is excellent in a property of preventing secondary staining. However, the hairdyes are completely removed by washing the hair, and naturally they do not have the persistent hair-dyeing performance.

In conventional temporary hairdyes, inorganic pigments such as carbon black have been used in many cases in order to raise intensity of the dyed colors. However, in hairdyes blended with a pigment having a specific gravity different from those of the vehicles, the pigment, which are the colorant, settles down or floats, so that the hairdyes have to be redispersed by stirring at the time of using, which is troublesome in use.

Restrictions such as providing hairdyes with a high viscosity are needed in order to prepare hairdyes which do not have to be redispersed. This results in less staining on the skin caused by dripping of an applied liquid when applied to the hair, but a cosmetic (hairdye) applied on the hair is "thickened", and a natural feeling of the hair after dyeing is notably damaged.

A cosmetic applicator equipped with an applying brush having a simple valve mechanism has so far been used as means for applying these cosmetics on the hair. However, not only an increased viscosity of the cosmetics makes it impossible in a certain case to sufficiently discharge the cosmetic by discharge force of the simple valve mechanism, but also "spreading" of the cosmetics on a brush, which is an applicator, is deteriorated, so that it has sometimes become difficult to apply a cosmetic (hairdye) on the deep part of the hair through the hair on the surface.

In addition thereto, as is usual in a dispersion (cosmetic) using a heavy inorganic pigment, it is difficult to design the dispersion (cosmetic), and resins used for providing the dispersion with a fixing property onto the hair are restricted. In developing cosmetics in which components to be used are regulated by the "The Japanese standards of cosmetic ingredients", such circumstance-makes it difficult to obtain cosmetics meeting the intended effects.

In light of such existing state, an object of the present invention is to provide a cumulative hair-dyeing temporary hairdye which has a function to gradually dye the hair by repeated use while a use method thereof is the same as that of a temporary hairdye and which is less liable to cause the colorant to secondarily stain a contacted matter when contacted in the state that the hair is not washed after dyeing and does not necessarily require washing of the hair after use.

DISCLOSURE OF THE INVENTION

Various investigations repeated by the present inventors in order to solve the problems described above have resulted in finding that the problems described above can be solved by a composition which does not contain an inorganic pigment as a colorant and which is prepared by blending an acid dye, a hair-dyeing aid, a lower alcohol and water with a nonionic or anionic silicone base resin, and thus the present invention has come to be completed.

That is, the present invention comprises:

(1) A cumulative hair-dyeing temporary hairdye comprising 0.01 to 3% by weight of an acid dye as a colorant, 0.1 to 10% by weight of a nonionic or anionic silicone base resin, 3 to 20% by weight of a hair-dyeing aid, 30 to 80% by weight of a lower alcohol and 5 to 50% by weight of water and having a pH of 2 to 5 and a viscosity of 100 mPa·s or less.

(2) The cumulative hair-dyeing temporary hairdye as described in the above item (1), wherein the silicone base resin is a block copolymer of polydimethylsiloxane with methacrylic acid and/or methacrylic acid alkyl ester.

(3) A hairdye constituted in such a manner that an inner barrel having a reservoir part for a hairdye is set movably in an axial direction in the inside of an outer barrel; a valve system which is opened by advancing the inner barrel against the outer barrel by means of a knocking member is allowed to intervene between an applying member having a comb which is mounted on the front edge of the outer barrel and the tip of the reservoir part; and a hairdye can be supplied from the tip of the inner barrel to the applying member, wherein the reservoir part in the applicator is charged with the cumulative hair-dyeing temporary hairdye as described in the above item (1) or (2).

(4) A production process for a cumulative hair-dyeing temporary hairdye, wherein the respective components as described in the above item (1) or (2) are blended in such an order that at least a nonionic or anionic silicone base resin and a lower alcohol are mixed to prepare a vehicle, and then blended with water and the other components and stirred.

BEST MODE FOR CARRYING OUT THE INVENTION

The present invention shall be explained below in details.

The acid dye used in the present invention shall not specifically be restricted as long as it is usually used for a temporary hairdye and a semi-permanent hairdye. To be specific, capable of being used alone or in a mixture of two or more kinds thereof are those prescribed in "ministerial ordinance prescribing tar colors which can be used for drugs" (announced by the Ministry of Health and Welfare in 1966) which do not have a harmful action to a human body and is authorized to be used for coloring drugs, quasi-drugs and cosmetics.

The specific examples of such acid dyes include Red No. 3 (Erythrosine), Red No. 102 (New coccine), Orange No. 205 (Orange II), Yellow No. 4 (Tartrazine), Yellow No. 402 (Polar Yellow 5G), Green No. 3 (Fast Green FCF), Green No. 204 (Pyranine Conc), Blue No.1 (Brilliant Blue FCF), Blue No.202 (Patent Blue NA), Purple No. 401 (Alizurol Purple), Brown No. 201 (Resorcin Brown) and Black No. 401 (Naphthol Black). However, they are merely few examples and shall not specifically be restricted. A blending amount of the acid dye is preferably 0.01 to 3% by weight, more preferably 0.02 to 1% by weight based on the whole composition. If it is less than 0.01% by weight, the hair-dyeing effect is not sufficiently exhibited, and if it exceeds 3% by weight, other things such as skin are liable to be stained.

The nonionic or anionic silicone base resin used in the present invention is used in order to prevent secondary staining, particularly to improve the water resistance. In this respect, the nonionic or anionic silicone base resin is a block copolymer of a nonionic monomer unit and/or an anionic monomer unit with a polysiloxane unit.

The polysiloxane unit is preferably polydimethylsiloxane.

The anionic monomer includes methacrylic acid, acrylic acid, itaconic acid, maleic acid and fumaric acid. Among them, methacrylic acid and acrylic acid are preferred. Further, the nonionic monomer includes aromatic hydrocarbons such as styrene and (meth)acrylic acid esters such as methyl methacrylate, ethyl methacrylate, butyl methacrylate, methyl acrylate, ethyl acrylate and butyl acrylate. Among them, esters of methacrylic acid and aliphatic alcohols having 6 or less carbon atoms are preferred, but they shall not be restricted to these compounds.

That is, the silicone base resin according to the present invention is particularly preferably a block copolymer of polydimethylsiloxane with methacrylic acid and/or an ester of methacrylic acid and an aliphatic alcohol having 6 or less carbon atoms. The block copolymer, the above silicone resin, is obtained by a synthetic process in which a nonionic monomer or an anionic monomer is added to a polysiloxane compound which is left polymerization activity at the terminals and they are polymerized. Usually, it is obtained by turning a polysiloxane compound into a living polymer in the presence of an anionic polymerization initiator and then copolymerizing the nonionic monomer or anionic monomer described above therewith.

A constitutional proportion of the polysiloxane compound contained in the block copolymer, the silicone base resin, shall not specifically be restricted and is preferably 10 to 80% by weight, more preferably 20 to 70% by weight. If it is 10% by weight or less, the feeling is deteriorated, and if it is 80% by weight or more, the solubility into a solvent such as water and lower alcohol is deteriorated. Accordingly, both ranges are not preferred.

Also, a number average molecular weight of the block copolymer shall not specifically be restricted, but too small a molecular weight deteriorates moisture resistance of the block copolymer and makes the color of the dyed hair liable to fade due to sweat or rain, so that it is preferably 50,000 or more, more preferably 60,000 or more.

A blending amount of the nonionic or anionic silicone base resin described above in the present invention is preferably 0.1 to 10% by weight, more preferably 0.5 to 5% by weight based on the whole composition. If it is less than 0.1% by weight, the secondary staining is not necessarily prevented, and if it exceeds 10% by weight, brought about is the inconvenience that the hair is too stiffly set in finishing after use.

Capable of being used as the hair-dyeing aid alone or in a mixture of two or more kinds thereof are those used for conventional acid hairdyes (semi-permanent hairdyes) such as benzyl alcohol, phenylethyl alcohol, phenoxyethanol, propylene glycol, N-methylpyrrolidone, gluconic acid lactone, levulinic acid, urea, ethylene carbonate, N-methyl-2-pyrrolidone, α-ketoglutaric acid, γ-butyrolactone, propionamide and acetic acid amide. Among them, benzyl alcohol and phenylethyl alcohol are preferred in terms of the hair-dyeing effect and the stability of the composition.

A blending amount thereof is preferably 3 to 20% by weight, more preferably 5 to 15% by weight based on the whole composition. If it is less than 3% by weight, the hair-dyeing effect is not sufficiently exerted, and if it exceeds 20% by weight, the drying property is reduced. Accordingly, both ranges are not preferred.

At least one of ethanol, propanol, butanol, isopropanol or isobutanol is used as the lower alcohol, and ethyl alcohol is preferred in terms of safety, a drying property and an odor.

A blending amount of the lower alcohol is preferably 30 to 80% by weight, more preferably 40 to 70% by weight based on the whole composition. If it is less than 30% by weight, the drying property is reduced, and if it exceeds 80% by weight, the hair-dyeing effect is not sufficiently exerted.

A blending amount of water is preferably 5 to 50% by weight, more preferably 10 to 35% by weight based on the whole composition. If it is less than 5% by weight, the hair can not sufficiently be swollen so that the hair-dyeing effect is reduced. On the other hand, if it exceeds 50% by weight, the drying property is reduced. Accordingly, both ranges are not preferred.

The temporary hairdye of the present invention has preferably a pH of 2 to 5, more preferably 2 to 4. If the pH is less than 2, the skin is stimulated in a certain case, and if it exceeds 5, the hair-dyeing effect is reduced.

In the present invention, the pH can be controlled by using organic acids such as formic acid, acetic acid, lactic acid, tartaric acid, malic acid, citric acid and glycolic acid, inorganic acids or salts thereof and, if necessary, alkalis.

The temporary hairdye of the present invention has a viscosity of 100 mPa·s or less, preferably 50 mPa·s or less and more preferably 10 mPa·s or less. If the viscosity exceeds 100 mPa·s, a large amount of the hairdye adheres to the hair, and the sticky state lasts. Further, the drying property is reduced, and therefore it is not suited for keeping the state as it is without washing the hair immediately after use.

In producing the cumulative hair-dyeing temporary hairdye in the present invention, the block copolymer of polydimethylsiloxane with methacrylic acid and/or a methacrylic acid ester used as the silicone base resin particularly causes coagulation or precipitation in water staying in an acid area which is an essential requisite in the present invention. In addition, once the resin coagulate, it can not be dissolved again by merely adding a lower alcohol which is a solvent for dissolving it. Accordingly, in producing the cumulative hair-dyeing temporary hairdye using the block copolymer of polydimethylsiloxane with methacrylic acid and/or a methacrylic acid ester as the silicone base resin, it is necessary to mix the block copolymer of polydimethylsiloxane with methacrylic acid and/or a methacrylic acid ester and the lower alcohol to prepare a vehicle and to blend it with water and the other components and then to stir and mix homogeneously them.

In this case, in order to prevent the block copolymer of polydimethylsiloxane with methacrylic acid and/or a methacrylic acid ester from being deposited to such an extent that a trouble is not caused to the embodiment, the proportion of the lower alcohol contained in the vehicle described above to water blended has to be larger than 3:5 in terms of a weight ratio of lower alcohol:water.

The blending order of the other components constituting the present invention shall not specifically be prescribed, and they may be blended at optional stages.

In using the hairdye according to the present invention, a pen type toilet vessel which has an applying member at a tip and is equipped with a valve mechanism for preventing a liquid from being discharged is desirable as the applicator used for the liquid having a low viscosity to sufficiently exhibit the expected effects.

Such pen type toilet vessel is constituted in such a manner that an inner barrel having a reservoir part for a hairdye is set movably in an axial direction in the inside of an outer barrel; a valve system which is opened by advancing the inner barrel against the outer barrel by means of a knocking member is allowed to intervene between an applying member having a comb which is mounted on the front edge of the outer barrel and the tip of the reservoir part; and the hairdye can be supplied from the tip of the inner barrel to the applying member through an absorber such as a sponge.

The cumulative hair-dyeing temporary hairdye of the present invention is charged into the reservoir part described above in the pen type applicator and applied, whereby the using system of the cumulative hair-dyeing temporary hairdye which is excellent in carrying and handling properties can be effectuated without causing "dripping" due to the low viscosity and unexpected discharge of the liquid while supplying the required hairdye to the applying part.

When using the composition of the present invention by means of such pen type toilet vessel, a liquid-applying part such as a brush equipped with a comb and a pen feed is preferably used as the applying member at a tip. The reason therefor is that the cumulative hair-dyeing temporary hairdye of the present invention has a relatively lower viscosity than those of conventional acid hairdyes so as not to need to wash the hair immediately after use and thus is likely to be applied not only to the hair but also to the head skin if used by the same using means as those of conventional acid hairdyes.

Those shown in, for example, FIG. 1 and FIG. 7 of Japanese Utility Model Publication No. Hei 8-4882 can suitably be used as the pen type toilet vessel. In this case, a means for opening a valve by advancing the inner barrel against the outer barrel may be a conventionally known knocking member as shown in FIG. 7 or an improved type system as shown in FIG. 1, wherein a non-circular head is provided at the tip of an inner barrel to inhibit the inner barrel from advancing with a barrier wall which is disposed at a position of a certain phase in a circumferential direction of the outer barrel, whereby a liquid is prevented from being unexpectedly discharged. In particular, the improved type system as shown in FIG. 1 of Japanese Utility Model Publication No. Hei 8-4882 is suited to the present invention. In this case, if an applying liquid is charged into a vessel with an applying member constituted by combining a liquid-applying part such as a brush and a pen feed with a comb and an absorber and used, the head skin can be avoided from being stained in use to the utmost, and the hairdye can be applied on the hair in the vicinity of the head skin (borders of the hair). The hairdye can temporarily be held in an absorber sufficiently by making the best use of the property of a low viscosity which the hairdye of the present invention has and thus can be applied in an optimum amount on the hair via an applying part such as a brush and a pen feed.

In the composition of the present invention, other components may suitably be blended as long as the effects of the present invention and the stability of the system are not damaged. They include, for example, various surfactants, preservatives, antioxidants, reduction preventives, chelating agents, UV absorbers, viscosity controlling agent, oil components, silicone derivatives, fragrances, animal and plant extracts and publicly known polymer components.

EXAMPLES

The present invention shall be explained below in details with reference to examples, but the present invention shall not be restricted by the following examples.

In the examples described below, a blending amount represents % by weight unless otherwise described.

Example 1

A silicone base resin of a block copolymer (a block copolymer of polydimethylsiloxane and methacrylic acid and/or a methacrylic acid ester; polydimethylsiloxane: 30%) and ethyl alcohol were mixed in a blending ratio shown below to prepare a vehicle, and water and the other components shown below were blended with the vehicle and homogeneously stirred and mixed to obtain a cumulative hair-dyeing temporary hairdye.

| | |
|---|---|
| Orange No. 205 | 0.20 |
| Silicone base resin of block copolymer | 0.50 |
| Lactic acid | 2.00 |
| Benzyl alcohol | 10.00 |
| Water | 30.00 |
| Ethanol | balance |

Example 2

Components shown below were blended in the same manner as in Example 1, except that phenylethyl alcohol was substituted for benzyl alcohol, and they were homogeneously stirred and mixed to obtain a cumulative hair-dyeing temporary hairdye.

| | |
|---|---|
| Orange No. 205 | 0.50 |
| Purple No. 401 | 0.10 |
| Black No. 401 | 0.20 |
| Silicone base resin of block copolymer | 2.50 |
| Lactic acid | 2.00 |
| Phenylethyl alcohol | 10.00 |
| Water | 30.00 |
| Ethanol | balance |

Comparative Example 1

The same procedure as in Example 1 was repeated to obtain a cumulative hair-dyeing temporary hairdye, except that the silicone base resin of the block copolymer was not blended.

| | |
|---|---|
| Orange No. 205 | 0.20 |
| Purple No. 401 | 0.10 |
| Black No. 401 | 0.20 |
| Lactic acid | 2.00 |
| Benzyl alcohol | 10.00 |
| Water | 30.00 |
| Ethanol | balance |

Comparative Example 2

The same procedure as in Example 1 was repeated to obtain a cumulative hair-dyeing temporary hairdye, except that an anionic vinyl acetate base resin was substituted for the silicone base resin of the block copolymer.

| | |
|---|---|
| Orange No. 205 | 0.20 |
| Purple No. 401 | 0.10 |
| Black No. 401 | 0.20 |
| Anionic vinyl acetate base resin | 2.50 |
| Lactic acid | 2.00 |
| Benzyl alcohol | 10.00 |
| Water | 30.00 |
| Ethanol | balance |

Comparative Example 3

The same procedure as in Example 1 was repeated to obtain a cumulative hair-dyeing temporary hairdye, except that an amphoteric polymer resin having a betaine group was substituted for the silicone base resin of the block copolymer.

| | |
|---|---|
| Orange No. 205 | 0.20 |
| Purple No. 401 | 0.10 |
| Black No. 401 | 0.20 |
| Amphoteric polymer resin having a betaine group | 2.50 |
| Lactic acid | 2.00 |
| Benzyl alcohol | 10.00 |
| Water | 30.00 |
| Ethanol | balance |

Five kinds of the cumulative hair-dyeing temporary hairdyes obtained in Examples 1 and 2 and Comparative Examples 1 to 3 were charged into the improved pen type toilet vessel equipped with a comb as shown in FIG. 1 of Japanese Utility Model Publication No. Hei 8-4882 to be evaluated in various product tests. Further, in respect to head skin staining, the hairdyes were charged into a commercially available acid hairdye vessel (a comb-tooth vessel in which a content is discharged from a discharge port of a comb tooth installed in the vessel body by grasping the vessel body to apply pressure and applied on the hair and in which provided is an air check valve mechanism for inhaling air into a base end part of a comb-tooth body) to carry out comparative evaluation.

Temporary hair-dyeing property: performance evaluation as a temporary hairdye after applying and drying the hairdyes.

Cumulative hair-dyeing property: evaluation of the cumulative hair-dyeing property after repeating three times applying and drying the hairdyes-washing the hair.

Secondary staining property: a filter paper wetted with water is pressed to the hair after applying and drying the hairdyes, and the staining property is evaluated by the degree of coloring the filter paper. No coloring is rated as good.

Head skin staining: evaluated by the degree of staining on the head skin in applying the hairdyes by each vessel.
Evaluation: ○: good
Δ: a little inferior
X: inferior

TABLE 1

| | Example | | Comparative Example | | |
|---|---|---|---|---|---|
| | 1 | 2 | 1 | 2 | 3 |
| Temporary hair-dyeing property | Δ | ○ | ○ | ○ | ○ |
| Cumulative hair-dyeing property | ○ | ○ | ○ | ○ | X |
| Secondary staining property | ○ | ○ | X | X | ○ |
| Head skin staining  Pen type toilet vessel equipped comb | ○ | ○ | ○ | ○ | ○ |
| Commercial vessel | X | X | X | X | X |

As described above, the cumulative hair-dyeing temporary hairdye of the present invention contains a nonionic or anionic silicone base resin, so that it does not have a secondary staining property and is improved particularly in water resistance. It exhibits a function to gradually dye the hair by repeated use. Further, displayed is the effect that the hair does not necessarily have to be washed after use.

Industrial Applicability

A method of using the hairdye of the present invention is the same as that of a temporary hairdye, but it has a function to gradually dye the hair by repeated use and is useful as a cumulative hair-dyeing temporary hairdye requiring no washing of the hair after use.

What is claimed is:

1. A cumulative hair-dyeing composition comprising 0.01 to 3% by weight of an acid dye as a colorant, 0.1 to 10% by weight of a nonionic or anionic silicone base resin, 3 to 20% by weight of a hair-dyeing aid, 30 to 80% by weight of a lower alcohol and 5 to 50% by weight of water, wherein an inorganic pigment is not contained and said composition has a pH of 2 to 5 and a viscosity of 100 mPa·s or less.

2. The cumulative hair-dyeing composition as described in claim 1, wherein the silicone base resin is a block copolymer of polydimethylsiloxane with methacrylic acid and/or methacrylic acid ester.

3. A hairdye apparatus constituted in such a manner that an inner barrel having a reservoir part for a hairdye composition is set movably in an axial direction in the inside of an outer barrel; a valve system which is opened by advancing the inner barrel against the outer barrel by means of a knocking member is allowed to intervene between an applying member having a comb which is mounted on the front edge of the outer barrel and the tip of the reservoir part; and a hairdye composition can be supplied from the tip of the inner barrel to the applying member, wherein the reservoir part in the applicator of the above pen type is charged with the cumulative hair-dyeing composition as described in claim 1.

4. A production process for the cumulative hair-dyeing composition as described in claim 1, wherein the respective components are blended in such an order that at least a silicone base resin, which is a block copolymer and a lower alcohol are mixed to prepare a vehicle, and then blended with water and the respective components described above and stirred.

5. A hairdye apparatus constituted in such a manner that an inner barrel having a reservoir part for a hairdye composition is set movably in an axial direction in the inside of an outer barrel; a valve system which is opened by advancing the inner barrel against the outer barrel by means of a knocking member is allowed to intervene between an applying member having a comb which is mounted on the front edge of the outer barrel and the tip of the reservoir part; and a hairdye composition can be supplied from the tip of the inner barrel to the applying member, wherein the reservoir part in the applicator of the above pen type is charged with the cumulative hair-dyeing composition as described in claim 2.

6. A production process for the cumulative hair-dyeing composition as described in claim 2, wherein the respective components are blended in such an order that at least a silicone base resin, which is a block copolymer and a lower alcohol are mixed to prepare a vehicle, and then blended with water and the respective components described above and stirred.

* * * * *